United States Patent [19]

Vértesi et al.

[11] Patent Number: 4,710,578

[45] Date of Patent: Dec. 1, 1987

[54] ISOTHIURONIUM SALTS

[75] Inventors: Csaba Vértesi; Attila Molnár; Lajos Guczoghy, all of Budapest, Hungary

[73] Assignee: Peremartoni Vegyipari Vallalat, Peremartongyartelep, Hungary

[21] Appl. No.: 809,888

[22] PCT Filed: Apr. 2, 1985

[86] PCT No.: PCT/HU85/00022

§ 371 Date: Nov. 25, 1985

§ 102(e) Date: Nov. 25, 1985

[87] PCT Pub. No.: WO85/04399

PCT Pub. Date: Oct. 10, 1985

[30] Foreign Application Priority Data

Apr. 3, 1984 [HU] Hungary .............................. 1324/84
Mar. 19, 1985 [HU] Hungary .............................. 1324/84

[51] Int. Cl.$^4$ .......................................... C07C 157/14
[52] U.S. Cl. .......................................... 558/4; 558/5; 514/508
[58] Field of Search ........................ 558/4, 5; 514/508

[56] References Cited

U.S. PATENT DOCUMENTS 4,017,539 4/1977 Bosies et al. .................... 260/501.14

FOREIGN PATENT DOCUMENTS 788429 10/1935 France ...................................... 558/5

*Primary Examiner*—Warren B. Lone

*Attorney, Agent, or Firm*—Karl F. Ross; Herbert Dubno; Jonathan Myers

[57] ABSTRACT

According to the present invention there are provided isothiuronium salts of the general Formula I

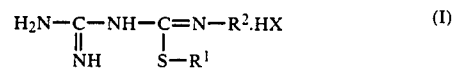

wherein
$R^1$ is $C_{1-6}$ alkyl, $C_{2-6}$ alkenyl, $C_{2-6}$ alkynyl, $C_{3-6}$ cycloalkyl, aralkyl or aryl, the said groups being optionally substituted by one or more hydroxy, mercapto and/or halogen;
$R^2$ stands for hydrogen, $C_{1-6}$ alkyl, $C_{2-6}$ alkenyl, $C_{2-6}$ alkynyl or $C_{3-6}$ cycloalkyl;
X represents an organic or inorganic anion/.

The compounds and salts of the present invention can be prepared by reacting a compound of the general Formula II

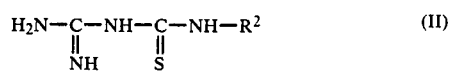

with an agent capable of introducing a $R^1$ group.

The compounds of the general Formula I exhibit antitumor and immunostimulant effect and are useful in therapy.

13 Claims, No Drawings

ISOTHIURONIUM SALTS

CROSS REFERENCE TO RELATED APPLICATIONS

This application is a national phase application based, in turn, upon a Hungarian application 1324/84 of 3 Apr. 1984 and a modification thereof of 19 Mar. 1985.

FIELD OF THE INVENTION

This invention relates to isothiuronium salts, a process for the preparation thereof and pharmaceutical compositions comprising the same. The majority of the said isothiuronium salts are new compounds. The said compounds possess useful antitumor and antistimulant, antiparasitic effect and can be used in human and veterinary therapy.

BACKGROUND OF THE INVENTION

Compounds of the Formula I

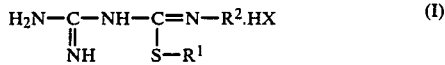

wherein $R^1$ is methyl, ethyl or benzyl and $R^2$ stands for hydrogen are known (French Pat. No. 788,429 and DOS No. 2,426,683). In these publications however the said compounds were only mentioned as intermediates and the publications were completely silent in disclosing any biological activity thereof or any use of these compounds in therapy.

DESCRIPTION OF THE INVENTION

According to an aspect of the present invention there are provided new compounds and salts of the Formula I

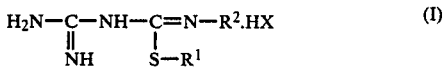

wherein
$R^1$ is $C_{1-6}$ alkyl, $C_{2-6}$ alkenyl, $C_{2-6}$ alkynyl, $C_{3-6}$ cycloalkyl, aralkyl or aryl, which groups can be substituted by one or more hydroxy, mercapto and/or halogen;
$R^2$ stands for hydrogen, $C_{1-6}$ alkyl, $C_{2-6}$ alkenyl, $C_{2-6}$ alkynyl or $C_{3-6}$ cycloalkyl;
X represents an organic or inorganic anion with the proviso that if $R^2$ stands for hydrogen, $R^1$ is other than methyl, ethyl or benzyl.

The term "$C_{1-6}$ alkyl" relates to straight or branched chain saturated aliphatic hydrocarbon groups (e.g. methyl, ethyl, n-propyl, isopropyl, n-butyl and isobutyl (etc.). The term "$C_{2-6}$ alkenyl" covers straight or branched chain olephinic unsaturated groups (e.g. vinyl, allyl and methallyl) (etc.). The term "$C_{2-6}$ alkynyl" relates to straight or branched chain aliphatic groups comprising at least one triple bond (e.g. propargyl) (etc.). The term "$C_{3-6}$ cycloalkyl" relates to cyclic saturated aliphatic hycrocarbon groups (e.g. cyclobutyl, cyclopentyl and cyclohexyl) (etc.). The term "aryl" group encompasses mono- and polycyclic aromatic hydrocarbon groups (e.g. phenyl and naphthyl) (etc.). The term "aralkyl" relates to alkyl groups substituted by at least one aryl group (e.g. benzyl, β-phenyl-ethyl) (etc.). The term "halogen" encompasses the fluorine, chlorine, bromine and iodine atoms.

The said alkyl, alkenyl, alkynyl, cycloalkyl, aryl and aralkyl groups may optionally bear one or more substituents selected from the group consisting of hydroxy, mercapto and halogen. Thus as examples of the said substituted groups the following groups may be mentioned: 2-chloro-ethyl, 3-bromo-propyl, 2-hydroxyethyl, 3-chloro-2-hydroxy-propyl etc.

A preferred group of the compounds of the Formula I are those derivatives in which $R^1$ is allyl.

A further preferred group of the compounds of the Formula I are those derivatives in which $R^1$ is 2-halogeno-ethyl.

$R^2$ stands preferably for hydrogen, methyl, ethyl, n-propyl, isopropyl, n-butyl, allyl or cyclohexyl.

X stands preferably for a halide anion, particularly for chloride, bromide or iodide.

Particularly preferred representatives of the compounds of the Formula I are pharmaceutically acceptable salts of the following derivatives:
N-aminoiminomethyl-S-methyl-isothiuronium salts;
N-aminoiminomethyl-S-propyl-isothiuronium salts;
N-aminoiminomethyl-S-allyl-isothiuronium salts;
N-aminoiminomethyl-S-(2-chloroethyl)-isothiuronium salts;
N-aminoiminomethyl-S-(1-chloro-2-hydroxy-propyl)-isothiuronium salts;
N-aminoiminomethyl-S-(3-chloro-propyl)-isothiuronium salts;
N-aminoiminomethyl-S-(2-hydroxyethyl)-isothiuronium salts; and
N-aminoiminomethyl-S-glycidyl-isothiuronium salts.

Further preferred compounds of the Formula I are the N-aminoiminomethyl-N'-alkyl-S-allyl-isothiuronium salts, particularly the corresponding N'-methyl, N'-ethyl, N'-n-propyl and N'-isopropyl compounds. According to a further aspect of the present invention there is provided a process for the preparation of compounds of the general Formula I and salts thereof which comprises (a) reacting a compound of the Formula II

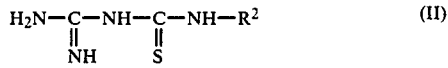

(wherein $R^2$ is as stated above) or a suitable salt thereof with an alkylating agent capable of introducing a $R^1$ group, preferably with an alkylating agent of the Formula $R^1$—Y (wherein $R^1$ is as stated above and Y stands for a leaving group, preferably halogen); or (b) reacting the compound of the Formula III

with a compound of the Formula $R^1$—SH (wherein $R^1$ is as stated above)

and if desired converting the product thus obtained into a salt by reacting with an acid of the Formula HX (wherein X is an anion of an organic or inorganic acid).

In the said reactions isothiuronium salts are formed. The reaction is generally accompanied by the formation of N-alkylated by-products.

According to a preferred form of realization of process a/ the starting materials of the Formula II are not used in the free base form but in the form of a suitable salt—particularly the carbonate—thereof. Thus the formation of the N-alkylated derivatives is quenched and this is probably due to the fact that the carbon dioxide evolved decreases the pH of the strongly basical medium.

As alkylating agent preferably the corresponding alkyl halides or dialkyl sulfates can be used, but other alkylating agents may be applied as well.

The reactants may be used in equimolar amount or the alkylating agent may be added in an excess. As reaction medium inert organic solvents, preferably an alcohol, aliphatic ketone, aliphatic nitrile or ether may be used.

The reaction may be accomplished under athmospheric pressure and at a temperature of 20°–80° C.

According to a preferred form or realization of method a/ the starting material of the Formula II and the alkylating agent are reacted in a molar ratio of 1:1–1:1.8, in anhydrous ethanol, acetonitrile, dimethyl formamide, acetone or ether, at a temperature between 20° C. and 30° C.

According to method b/ the compounds of the Formula IV

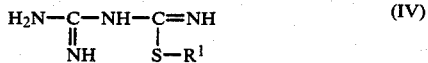

(which form a narrower sub-group of the compounds of the general Formula I; $R^2$ is hydrogen) may be prepared by reacting the compound of the Formula III with a thio-alcohol of the Formula $R^1$—SH. The reactants may be used in an equimolar amount or the thioalcohol of the general Formula $R^1$—SH may be applied in an excess. As reaction medium preferably an alcohol—particularly ethanol—may be used. The reaction may be accomplished under pressure, if necessary. It is preferred to work under a pressure of 1–5 bar and at a temperature of 20°–100° C.

The starting materials of the Formula II are known or can be prepared by methods known per se. Thus N-aminoiminomethyl-thiourea can be readily prepared by reacting dicyane diamide with hydrogen sulfide (Houben-Weyl VIII., 214). The N-aminoiminomethyl-N'-alkylthiourea derivatives of the Formula II can be prepared by reacting guanidine base with the corresponding alkyl isothiocyanate (U.S. Pat. No. 4,009,163).

The starting material of the Formula III can be prepared by known methods.

The product thus obtained can be converted into a pharmaceutically acceptable salt formed with an organic or inorganic acid. For salt-formation preferably formic acid, lactic acid, citric acid, maleic acid or sulfuric acid, hydrochloric acid, phosphoric acid or hydrobromic acid may be used.

The compounds of the Formula I possess antitumor and antiparasital immunostimulant properties. The strength and direction of the activity and the toxicity depend on the substituents of the molecule.

It is known that gutimine which is structurally related to the compounds of the general Formula I was tested as antihypoxial agent [C.A. 66 452,929 (1972); Pathol. Phys. Exp. Ther. 10, (6)] in pharmacological and clinical tests as substance causing microcirculation disorders [Gematol. Transfusiol. (1984), 29 (1), 49–52].

It has been found that the compounds of the Formula I are capable of restoring the decreased natural immune system of organism to the normal value or of increasing the same above the normal level.

Thus the organisms of animals and humans possess an immune system (e.g. tumor eliminating system). Once the activity of the this system is reduced or stops functioning, various diseases and tumors appear and manifest themselves. The compounds of the Formula I activate the natural immune systems and are thus useful in all cases when the increase of the reduced activity of the immune system and the further raising of the normal activity thereof is desired.

The compounds of the Formula I exhibit further useful biological effects, e.g. the curing of microcirculation disorders, binding of radicals detrimental to health, improvement of the function and lengthening of the lifetime of cells in an oxygen-deficient stage.

The biological activity of the compounds of the Formula I is demonstrated by the following tests. It is stated however that not all effects of the highly active compounds are shown.

TESTING OF SPECIFIC EFFECTS

Immunological Tests

Lymphocytes:

Lymphocytes were separated on Ficoll-Uromiro (Böyum 1968) gradient from the venal blood of healthy donors and patients suffering from malignant lymphoma and metastatizing solid tumours, respectively. When selecting the patients belonging to the latter group, the decreased ADCC and NK activity was taken into consideration. The phagocytes were removed by treatment with iron powder and a magnet.

ADCC:

ADCC was determined according to the method of Perlmann and Perlmann (1970) with minor modifications (Láng et al, 1981). Chicken erythrocytes labelled with $10^5$ $^{51}Cr$ and coated with anti-chicken erythrocyte rabbit-serum were incubated with the lymphocytes for 4 hours at 37° C. The reaction having been stopped the activity of the supernatant of the centrifuged cells was determined in a gamma-counter. The rate of chrome-release was expressed as the cytotoxicity index (CI %). This value was calculated as described in one of our earlier publications (Láng et al., 1980)—(see Table I).

NK:

NK activity was determined by the method of Jondal and Pross (1975) by using minor modifications (Láng et al, 1981). K-562 tumor cells labelled by $^{51}Cr$ were incubated with effector cells in a TC 199 liquid nutrient medium comprising 10% of decomplemented calf serum. The reaction having been stopped the radioactivity of the superntant of the centrifuged cells (chrome release) was counted in a gamma-counter. The killing of the tumor cells (cytotoxicity index %) was expressed as the difference of the test release and spontaneous release.

Statistical calculations were carried out by means of a mono-sample test. Several compounds of the general Formula I exhibit outstanding immunostimulant effect (e.g. compounds prepared according to Examples 11, 12 and 16). The said compounds are capable of significant increase of normal and strongly decreased NK and K cell activity, even above the normal level. The said effect may be so strong that cytotoxic activity decreased to one-tenth of the original value may be restored to the oroginal level (Table II).

In the dose range corresponding to the expected human plasma concentration the compounds of the general Formula I increase the NK and K cell activity of human lymphocytes and enhance NCMC and ADCC reaction, respectively at a dose-dependent rate. According to preliminary results of further immunological tests the compounds increase bastos transformation and migration.

On carrying out substitution on the nitrogen atoms the molar proportional immunostimulant effect related to the toxicity is generally decreased.

Since the cytotoxic activity of patients suffering from tumor is decreased proportionally with the stage of the disease and moreover it is further reduced by usual cytostatic treatments, it is of outstanding importance that the compounds of the Formula I possess strong immunostimulant effect and are not immunodepressors. This may be highly significant from the point of view of reconvalescence.

Migration of Leucocytes

Spontaneous (random) migration of leukocytes was measured on agarose microdrops according to the method of McCoy et al (1977) by carrying out some minor modifications (Kalmár and Gergely, 1982).

2 ml agarose drops (0.2%) were placed on migration plates (Greiner, German Federal Republic). TC 199 liquid nutrient medium was added and the plates were air-tightly closed. After 24 hours the migration area were measured under a stereomicroscope. The migration area were expressed in mm$^2$.

Migration of Leucocytes

The direct (random) migration of polymorphonuclear cells of healthy donors was increased by compounds according to Examples 11, 12 and 14. The optimal dose amounted to 1.0 µg/ml. At a higher dose (10 µg/ml) the effect was less expressed (Table III).

Mitogen-Induced Blastos Transformation

Lymphocytes were cultivated in a TC 199 liquid nutrient medium completed by 10% decomplemented calf serum, antibiotics and 25 mH HEPES (Serva). 200 µl of a cell suspension comprising $2.10^5$ lymphocytes were placed on a microplate (manufacturer: Sterilin Great Britain); five parallels were carried out each.

2 and 10 µg/ml, respectively of Phytohaemagglutinine (Leucoagglutinine; manufacturer Pharmacie Sweden) and 25 µg/ml of Concanavalin A (Carbiochem) were added to the cultures; the above values relate to final concentration. The cultures were cultivated at 37° C. for 72 hours. Eight hours before the termination of the end of the cultivating period 0.5 µCi $^3$H thymidine (Chemapol. Czechoslovakia) was added to the samples. Incubation was stopped by freezing the cultures. After melting the samples were filtered on an automatic harvester (Dynatech). The radioactivity of the samples was measured in a scintillation counter. The activity was expressed as c.p.m. (Tables IV and V).

Statistical Analysis

Significance was determined by means of a monosample 2T2 test. The results obtained with the product of Example 11 are disclosed in Tables I, II and III.

Preliminary Rapid Test for the Determination of Antitumor and Immunostimulant Effect This method was elaborated in our laboratories for the rapid testing of a large number of samples. CFLP male mice (average body-weight 30 g) were i.p. inoculated with four million ascites lymphoma cells.

In the test those animals were used on which on the fourth day an easily visible tumor—i.e. ascites—was developed. At least ten animals were used in each group and the mice were orally treated with one-tenth of the $LD_{50}$ value.

24 hours after oral treatment the results were evaluated by means of Giemsa stained ascites smear on the basis of cytological analysis. In the control group the same number of animals was used as in the treated group.

The damages of the tumor cells, the activation of the organism and the eventual toxical effects were evaluated.

On evaluating anti-tumor effect the percental ratio of killed and intact tumor cells was evaluated. The results were expressed according to the following scale:

| Killing rate of tumor cells | Effect |
|---|---|
| 0–30% | no effect |
| 30–70% | medium effect |
| 70–100% | strong effect /inhibition/ |

The increase of the immune system of the organism was evaluated on the basis of the number and activity of neutrophilic granulocytes, lymphocytes and macrophages appearing among the ascites tumor cells and participating at the immune system. The activity of the immune system is also manifested by the rate in which the above cells in the ascites form plasma-bridge bond with the tumor cells. According to this evaluation if there is no difference in the number and activity of the said cells, no increase can be declared over the control. Medium effect is observed if the increase of cell number or activity over the control amounts to 20%. The effect is strong if the increase of the cell number and activity of the immune system is more than 20% higher than the control (Table VII).

Toxicity was determined by evaluating the morphological changes of neutrophylic granulocytes and limphocytes, the vasquolization of plasma, the fragmentation of the nucleus, the formation of polysegments and toxical granulation. The toxicity was expressed by the following scale:

| Results observed | Toxicity |
|---|---|
| No above changes in own cells | no toxicity |
| 20% change | medium toxicity |
| changes above 20% | high toxicity |

TESTING OF ANTITUMOR EFFECT

1. In Vitro

K-562 human erythroleukamia cells and P-388 mouse lymphoma cell cultures were treated with 1–100 µg/ml of the test material.

2. In Vivo (a) NK-ly-ascites lymphoma

One million of Németh-Kellner ascites lymphoma cells were i.p. transplanted into twenty CFLP male mice (average bodyweight 30 g); [A new mouse ascites tumor to be used as a screening tool. Neoplasma 8, 337 (1961)]. Half of the animals served as control and the other half was treated with one-tenth of the $LD_{50}$ value of various compounds of the general Formula I p.o. and i.p. on one and five consecutive days, respectively. (If one-tenth of the $LD_{50}$ value was effective a lower dose was used). In the group subjected to one treatment the cytomorphological determination of the ascites smear was carried out after 24 hours and the ratio of damaged and killed cells, respectively was evaluated. In the groups treated for 5 days the survival rate was determined.

(b) $L_{1210}$ tumor $10^6$ $L_{1210}$ tumor cells were transplanted i.p. into twenty $BDF_1$ female mice (body weight 20 g). Treatment was started 24 hours after tumor transplantation and was continued for eight days. Each group consisted of 5 animals; dose: 5, 50 and 500 mg/kg p.o. daily. The control group also consisted of 5 animals. The rate of survival was observed.

(c) Lewis long tumor

In each group 6 animals were used. Dose: 5 and 50 mg/kg. The control group also consisted of 6 animals. In the test $C_{57}Bl$ female mice (weight 20 g) were used.

Tumor was s.c. transplanted into the muscle of the right leg. After 10 days the leg was amputated, the oral treatment was started and continued for 9 days. The animals were sacrificed and the metastases were counted under stereomicroscope.

(d) Dogs belonging to various species and having spontaneous mammal tumor (ductus cc.) were treated for 4 weeks with 1–10 mg/kg oral doses of the test materials. Test excision was performed and tissue samples were collected for hystological analysis.

Compounds according to Example 11, 13, 14, 15, 27, 28, 34, 35, 36, 38 exhibit an outstanding antitumor effect. Thus the compound according to Example 11 inhibits the K-562 human erythroleukaemia cells in tissue culture in a concentration of 4 µg/ml. On the other hand this compound inhibits the proliferation of P-388 cells only in a concentration of 40 µg/ml and when increasing the concentration to 400 µg/ml the activity does not become stronger. Compounds having a strong activity exhibit a dose-dependent effect in a concentration range of 0.5–5 µg/ml, while compound having a low activity are not dose-dependant. According to in vivo tests the members of this compound group are active against $L_{1210}$ either not at all or but to a very small extent.

The compounds significantly decrease the number of lung metastasis in Lewis long tumor. Compounds 11, 13, 14, 15, 22, 27, 28, 45 are effective in a dose lower than one-tenth of the $LD_{50}$ value. Compound according to Example 14 decreases by 50% the number of lung metastasis already in a dose of 5 mg/kg and this result is particularly significant in view of the fact that $LD_{50}=2380$ mg/kg.

It has been found that the effect can be strengthened to a larger extent by repeating the treatment than by increasing the dose.

Compounds according to Examples 11, 13, 14, 20, 22, 27, 45 proved to be active agains Nk-ly-ascites tumor in a concentration below one-tenth of the $LD_{50}$ value. The latter compounds increase survival rate and lifetime in a dose-dependant manner. These compounds exhibit immunostimulant effect in small doses, while in higher doses the direct antitumor effect manifests itself as well. Thus compounds of Example 11 and 22 exhibit an immunostimulant effect in doses of 25 mg/kg and 20 mg/kg, respectively. Compounds of Example 11 and 22 are cytotoxical in a dose range of 250–500 mg/kg and 40–160 mg/kg, respectively. S-allyl-, S-1-chloro-2-hydroxy-propyl- or S-1-bromo-2-hydroxy-propyl-substituted compounds of the general Formula I are highly active against spontaneous mammal tumors on dogs. In biopsy taken after treatment carried out for 3–4 weeks, cell infiltration of invasive character was observed in tumors (ductus cc.) consisting of lymphocytes and neutrophilic granulocytes, macrophages and occasionally of eosiniphilic granulocytes. On the tumor cells degenerative changes and strong decomposition was observed.

NK cells form plasma bridge bonds with tumor cells and this causes vacular degeneration of the plasma of tumor cells and large thinning in the DNS stand of the nucleus. The nucleus-plasma relation is changed, the nucleus are strongly swelled and the basophility of the plasma is decreased.

In about one-fourth of the cases the leukocyte infiltration in the tumor is negligible; on the other hand the tumor cells are swelled and hyalinially degenerated. In the intercellular stand a very large amount of hyaline stained material is deposited.

On administering the compound of Example 11 in an oral daily dose of 30–120 mg (0.5–2 mg/kg) for 6–12 months a significant improvement or reconvalescence respectively, was observed in human bone metastasis of mammal tumors, ovary tumors and pancreas tumors.

Testing of Antitumor Effect in Combinations (1) Combinations with known cytostatic agents Various cytostatic agents having biological alkylating effect were administered together with compounds of the Formula I to CFLP mice having NK-yl ascites tumor. The cytostatic agents were administered orally, intraperitonally or intravenously in a dose corresponding to one-fifth or one-tenth of the $LD_{50}$ value or in the most effective dosage disclosed in prior art. Compounds of the general Formula I were administered orally in a dose of one-tenth or one-twentieth of the $LD_{50}$ value once or several times, 48 hours after treatment with the cytostatical agent. Thus the combinations of cyclophosphamide, carnomustine, degranol, dibromo dulcitol and dibromo mannitol on the one hand and compounds of Examples 11, 13 on the other 14, 15, 16, 27, 28, 45 were administered. Compared to the control group treated only with the known cytostatic agent, the antitumor effect was strengthened and immunodepression decreased.

(2) Combination with known vitamins

The isothiuronium salts of the Formula I can be effectively combined with medium doses of vitamins A and $D_3$ and with high doses of vitamin C. Good results were obtained both in pharmacological tests and human clinical cases.

(3) Combination with known hormones

In the treatment of hormone-dependent tumors the combination proved to be useful both in pharmacological tests and human clinical cases.

(4) Use in surgery

The compounds of the general Formula I were successfully used in pharmacological tests in the case of solid tumors for surgical pre- and post-treatment (NK-ly solid, Yosida). It can be stated on the basis of pharmacological tests that the compounds of the Formula I are probably also suitable for use in human surgery for pre- and post-treatment.

Testing of Anti-Parasital Effect

Compounds of the Formula I were added orally to dogs infected by ticks (Ixodes ricinus) for three days. Thus N-aminoiminomethyl-S-allyl-isothiuronium hydrochloride was administered in an oral dose of 1-2 mg/kg and the killing rate of ticks was registered. Six--eight hours after administration of the active ingredient of the general Formula I all ticks were killed in the dogs.

Binding of Free Radicals

Compounds of Examples 9, 10, 11, 16, 23 and 29 significantly decrease the toxicity ($LD_{50}$) of hydrogen peroxide, organic peroxides and biological alkylating (free radical forming) agents. On the basis of their favorable toxicity data the compounds of the Formula I are more suitable for the binding of free radicals and protection against radiation than the known isothiuronium derivatives obtained from the corresponding thiourea. Thus the therapeutical effect of compound of Example 23 is better than that of beta-aminoethyl-isothiuronium hydrochloride.

Cardioprotective Effect in Isoprenaline Necrosis 5 mg/kg of isoproterenol are i.p. administered to male CFY rats (weight 250-300 g). In each group 10 animals were used. One part of the animals served as control and the other were treated with a 1-5 mg/kg i.p. or 10-50 mg/kg p.o. dose of compound No. 14. After two weeks the hearts were subjected to hystological evaluation. The ratio of necrotized and intact area of heart muscle were determined. It has been found that all treatments with N-aminoiminomethyl-S-allyl-isothiuronium hydrochloride of the general Formula I resulted in a significant decrease of necrosis.

On the damaged area the test compound presumably exhibits the effect thereof through the binding of hydrogen peroxide produced by neutrophilic granulocytes. On this model other free radical binding and antioxidant molecules exert a similar effect.

Effect on Circulation and Respiration

The compound according to Example 11 does not considerably effect the hemodinamical parameters and respiration function of cats with opened and closed chest, when administered in an i.v. dose of 10 mg/kg. The following parameters were tested: ventricular and peripherial pressure, heart frequency (action) ECG, volume/minute, contractility, respiratory volume, respiration rate and resistance. In a intravenal dose above 10 mg/kg the left venticular pressure and frequency decreased. In a dose of 50 mg/kg these effects were significant and long-lasting. In an i.v. dose of 100 mg/kg strong hemodynamical changes were observed but the cats did not perish. Effects of N-/aminoiminomethyl/-S-allyl-isothiuronium salts (halogenides). (Compound A)

TABLE I

Effect on ADDC. Cytotoxicity index /%/.
Ratio of effector cells; aimed cells = 5:1. Incubation time 4 hours.
Average: ±S.E.

| Group /case number/ | Control | Treatment | | |
|---|---|---|---|---|
| | | Compound A | /M.w.: 194,7/ | |
| | | $6.7 \times 10^{-10}$ mole | $6.7 \times 10^{-9}$ mole | $6.7 \times 10^{-8}$ mole |
| Normal ADCC /10/ | 42.0 ± 5.0 | 58.5 ± 5.2 +39% | 64 ± 5.8 +52% | 68.2 ± 5.3× +62% |
| Decreased ADCC /10/ | 2.8 ± 0.8 | 6.35 ± 1.7 +126% | 7.7 ± 1.9 +175% | 10.2 ± 2.7× +264% |

× significant /$p < 0.05$/

TABLE II

Effect on NK activity.
Ratio of effector cells: aimed cells = 50:1.
Incubation time 4 hours.
Cytotoxicity index /%/. Average values: ± S.E.

| Group /case number/ | Control | Treatment [mole/ml] | | |
|---|---|---|---|---|
| | | Compound A | /M.w.: 194.7/ | |
| | | $6.7 \times 10^{-10}$ mole | $6.7 \times 10^{-9}$ mole | $6.7 \times 10^{-31\ 8}$ mole |
| Normal NK /8/ | 32.9 ± 2.5 | 41 ± 2.9 +25% | 43.4 ± 2.7 +32% | 47.6 ± 1.4 +45% |
| Decreased NK /7/ | 15.1 ± 2.4 | 21.6 ± 3.0 +43% | 25.3 ± 3.2 +68% | 32.2 ± 3.2× +113% |

× significant /$p < 0.05$/

TABLE III

In vitro effect on direct /random/ migration of human polymorphonuclear leucocytes. Migration area /$mm^2$/.
Average values of seven healthy controls: ± S.E.M.

| Treatment | Control | Dose [µg/ml] | | |
|---|---|---|---|---|
| | | 0.1 | 1.0 | 10.0 |
| Compound A | 10.02 ± 1.65 | 10.51 ± 1.22[1] | 12.25 ± 1.58[2] | 11.24 ± 1.69[2] |

[1] non significant
[2] significant /$p < 0.01$/
[3] significant /$p < 0.05$/.

TABLE IV

In vitro effect on blastos transformation of human lymphocytes stimulated by PHA and Con A. Healthy controls of normal reactivity; n = 6. Average c.p.m. ± S.E.M.

| Mytogenic agent | Control | Dose [µg/ml] | | |
|---|---|---|---|---|
| | | 0.1 | 1.0 | 10.0 |
| PHA 2 µg/ml | 21166 ± 3774 | 22233 ± 3688 | 23156 ± 2737 | 25404 ± 2860 |
| PHA 10 µg/ml | 29959 ± 4051 | 29969 ± 3557 | 33826 ± 3638 | 33790 ± 5203 |
| Con A 25 µg/ml | 10545 ± 3414 | 10564 ± 3764 | 14089 ± 2602 | 17038 ± 3202 |

TABLE V

In vitro effect on blastos transformation of human lymphocytes stimulated by PHA and Con A. Patients of decreased reactivity /tumor and SLE/; n = 6. Average c.p.m. ± S.E.M.

| Mytogenic agent | Control | Dose [µg/ml] | | |
|---|---|---|---|---|
| | | 0.1 | 1.0 | 10.0 |
| 1. Compound A | | | | |
| PHA 2 µg/ml | 3034 ± 1293 | 2877 ± 984 | 4344 ± 1153 | 4716 ± 1287 |
| PHA 10 µg/ml | 5267 ± 1392 | 5802 ± 1504 | 6323 ± 1161 | 6968 ± 1669 |
| Con A 25 µg/ml | 804 ± 307 | 1097 ± 354 | 935 ± 363 | 1023 ± 361 |

TABLE VI 24 hours' acute toxicity of compounds of the Formula I

| Example No. | $R^2$ | $R^1$ | LD$_{50}$ mg/kg p.o. | LD$_{50}$ mg/kg i.p. |
|---|---|---|---|---|
| 9 | H | methyl | 2320 ± 220 | |
| 23 | H | ethyl | 3080 ± 290 | |
| 10 | H | propyl | 2800 ± 260 | |
| 25 | H | butyl | 2700 ± 310 | |
| 24 | H | i-propyl | 2260 ± 210 | |
| 26 | H | i-amyl | 2260 ± 241 | |
| 13 | H | 2-chloroethyl | 1120 ± 140 | |
| 27 | H | 2-bromo-ethyl | 1050 ± 280 | |
| 14 | H | 1-chloro-2-OH—propyl | 1240 ± 160 | |
| 15 | H | 3-chloro-propyl | 1210 ± 180 | |
| 28 | H | 3-bromo-propyl | 980 ± 640 | |
| 16 | H | 2-hydroxy-ethyl | 3280 ± 460 | 1680 ± 210 |
| 29 | H | 1-oxypropyl | 2860 ± 180 | |
| 11 | H | allyl | 2380 ± 320 | 320 ± 30 |
| 44 | H | methallyl | 1640 ± 210 | |
| 18 | H | benzyl | 2420 ± 260 | |
| 17 | H | propargyl | 90 ± 7,6 | |
| 20 | methyl | allyl | 600 ± 54 | 75 ± 6.3 |
| 34 | ethyl | allyl | 780 ± 62 | 84 ± 7.6 |
| 22 | cyclohexyl | allyl | 450 ± 51 | 65 ± 5.1 |
| 21 | isopropyl | allyl | 280 ± 26 | 32 ± 4 |
| 45 | allyl | allyl | 380 ± 41 | 36 ± 4 |
| 22 | cyclohexyl | allyl | 400 ± 38 | 40 ± 6 |

TABLE VII

| Test compound Example No. | Antitumor effect | Immunostimulant effect | Toxic effect |
|---|---|---|---|
| 9 | medium | medium | medium |
| 23 | medium | strong | 0 |
| 10 | medium | medium | 0 |
| 25 | medium | medium | 0 |
| 24 | medium | medium | 0 |
| 26 | medium | medium | 0 |
| 13 | strong | weak | 0 |
| 27 | strong | weak | 0 |
| 14 | strong | weak | 0 |
| 15 | strong | weak | 0 |
| 28 | strong | weak | 0 |
| 16 | medium | strong | 0 |
| 29 | medium | medium | 0 |
| 11 | strong | strong | 0 |
| 44 | medium | medium | 0 |
| 18 | increase | 0 | 0 |
| 17 | weak | weak | medium |
| 20 | strong | weak | 0 |
| 34 | medium | medium | 0 |
| 22 | strong | weak | 0 |
| 21 | strong | weak | 0 |
| 45 | strong | weak | 0 |
| 22 | weak | weak | 0 |

According to a still further feature of the present invention there are provided pharmaceutical compositions comprising as active ingredient at least one compound of the Formula I (wherein $R^1$ is $C_{1-6}$ alkyl, $C_{2-6}$ alkenyl, $C_{2-6}$ alkynyl, $C_{3-6}$ cycloalkyl, aralkyl or aryl, the said groups being optionally substituted by one or more hydroxy, mercapto and/or halogen;

$R^2$ stands for hydrogen, $C_{1-6}$ alkyl, $C_{2-6}$ alkenyl, $C_{2-6}$ alkynyl or $C_{3-6}$ cycloalkyl;

X represents an organic or inorganic anion.

The pharmaceutical compositions of the present invention can be prepared by methods of pharmaceutical industry known per se. The active ingredients of the Formula I can be preferably finished in the form of capsules in admixture with conventional generally used auxiliary agents (lubricating agents etc.); the capsules may be manufactured by using automatical encapsulating machines. The pharmaceutical compositions can also prepared in the form of powder ampouls, parenteral compositions for injection and infusion purposes; these compositions may also prepared by methods known per se. As solvent e.g. distilled water or physiological saline solution can be used.

The active ingredients of the Formula I can also be finished in the form of an ointment, particularly as lypophilic ointments. Active ingredients of the Formula I having a stronger odor may be preferably finished by means of microencapsulation, e.g. by means of the formation of cyclodextrin inclusion complexes.

The pharmaceutical compositions of the present invention may also contain in addition to the compound of the Formula I one or more of known biologically active substances as active ingredient.

The pharmaceutical compositions of the present invention can be used both in human and veterinary therapy. When used as immunostimulant the oral or rectal dose may be preferably about 0.5–25 mg/kg. For local treatment it is preferred to apply higher doses.

INDUSTRIAL APPLICABILITY

The invention relates to predominantly new compounds having antitumor and immunostimulant effect.

MODES OF CARRYING OUT THE INVENTION

Further details of the present invention are to be found in the Examples without limiting the scope of protection to the said Examples.

STARTING MATERIALS

EXAMPLE 1

N-Aminoiminomethyl-Thiourea Carbonate 84.0 g (1.0 mole) of dicyan diamide and 300 ml of water are filled into an autoclave. Into the closed autoclave 34.0 g (1 mole) of gaseous hydrogen sulfide are introduced in the following manner: at a temperature of 20° C. so much hydrogen sulfide gas is introduced that the pressure in the autoclave amounts to 1.5 bar. The introduction of gas is stopped and the autoclave is slowly heated to 80° C. In the mean time the gaseous hydrogen sulfide is introduced at such a rate that the pressure in the autoclave should be constantly 1.5 bar. After the complete amount of hydrogen sulfide gas is introduced the autoclave is kept at 80° C. until the pressure decreases to 0.3–0.4 bar. The reaction mixture is cooled to 20° C., flushed with nitrogen and filtered. The clear filtrate is cooled to 0° C., and carbon dioxide gas is let in. The precipitated white crystalline N-(aminoiminomethyl)-thiourea carbonate is filtered off, washed with cold water and dried at 60°–80° C. Thus 100 g of the desired compound are obtained, yield 67%, mp.: 127°–129° C.

The IR spectrum of the product thus obtained is compared with that of the standard sample of the compound.

EXAMPLE 2

N-Aminoiminomethyl-N'-Methyl-Thiourea Carbonate

To a solution of 5.9 g (0.1 mole) of guanidine base and 30 ml of acetone a solution of 7.3 g (0.1 mole) of methyl isothiocyanate in 10 ml of acetone is added. The isothiocyanate solution is added at such a rate to the guanidine solution that the temperature of the mixture should not exceed 40° C. The reaction mixture is allowed to stand at 40° C. for 4 hours, whereupon the solvent is removed in vacuo. The residual light yellow oil is suspended in water to yield an opalescent solution. Carbon dioxide gas is introduced into the solution thus obtained and the desired compound precipitates in the form of white crystals.

Yield: 12.0 g /73.5%/. Mp.: 132°–134° C.

EXAMPLES 3-8

In an analogous manner to Example 2 the following compounds are prepared:
3. N-aminoiminomethyl-N'-ethyl-thiourea-carbonate
4. N-aminoiminomethyl-N'-n-propyl-thiourea-carbonate
5. N-aminoiminomethyl-N'-isopropyl-thiourea-carbonate
6. N-aminoiminomethyl-N'-n-butyl-thiourea-carbonate
7. N-aminoiminomethyl-N'-allyl-thiourea-carbonate
8. N-aminoiminomethyl-N'-cyclohexyl-thiourea-carbonate In the following Examples the preparation of the end-products of the Formula I is disclosed.

EXAMPLE 9

N-Aminoiminomethyl-S-Methyl-Isothiuronium Iodide 14.9 g /0.05 mole/ of N-aminoiminomethyl-thiourea carbonate are suspended in 50 ml of anhydrous ethanol. To the suspension thus obtained 17.0 g /0.12 mole/ of methyl iodide are added. The reaction mixture is slowly heated to boiling, whereby carbon dioxide is evolved. The reaction mixture is heated to boiling for 30 minutes and cooled to room temperature. The mixture is filtered in order to remove the eventual crystalline precipitate. The clear filtrate is evaporated in vacuo and the residual oil is recrystallized from ethyl acetate. The yellow crystals are filtered off and dried at 40°–50° C. Thus 22.1 g of the desired compound are obtained, yield 85%, mp.: 124°–125° C.

EXAMPLE 10

N-Aminoiminomethyl-S-n-Propyl-Isothuronium Bromide 14.9 g /0.05 mole/ of N-aminoiminomethyl-thiourea carbonate are suspended in 50 ml of anhydrous ethanol. To the suspension 14.8 g /0.12 mole/ of n-propyl bromide are added. The reaction mixture is slowly heated to boiling under stirring, whereby carbon dioxide is evolved. The reaction mixture is heated to boiling for 45 minutes, and cooled to room temperature. The mixture is filtered in order to remove the eventually precipitated substance. The clear filtrate is evaporated in vacuo and the oily residue is crystallized from ethyl acetate. The white crystals are filtered and dried at 40°–50° C. Thus 19.5 g of the desired compound are obtained, yield 81%. Mp.: 122°–124° C.

EXAMPLE 11

N-Aminoiminomethyl-S-Allyl-Isothiuronium Bromide 14.9 g (0.05 mole) of N-aminoiminomethyl-thiourea carbonate are added to 50 ml of anhydrous ethanol. To the suspension thus obtained 14.5 g (0.12 mole) of allyl bromide are added. The reaction mixture is slowly heated to boiling under vigorous stirring. The reaction mixture is refluxed for 30 minutes and cooled to room temperature. The mixture is filtered in order to remove the eventually precipitated substance. The filtrate is evaporated in vacuo and the oily residue is crystallized from ethyl acetate. The precipitated crystals are filtered and dried at 40°–50° C. Thus 19.6 g of the desired compound are obtained, yield 82%. Mp.: 123°–125° C.

EXAMPLE 12

N-Aminoiminomethyl-S-Allyl-Isothiuronium Chloride 14.9 g (0.05 mole) of N-aminoiminomethyl-thiourea carbonate are added to 50 ml of anhydrous ethanol. To the suspension thus obtained 9.18 g (0.12 mole) of allyl chloride are added and the reaction mixture is slowly heated to boiling under vigorous stirring. The reaction mixture is refluxed for an hour and cooled to room temperature. The mixture is filtered in order to remove the eventually precipitated substance. The filtrate is evaporated in vacuo. The oily residue is crystallized from ethyl acetate. The precipitated crystals are filtered and dried at 40°–50° C. Thus 15.7 g of the desired compound are obtained, yield 81%, mp.: 125°–127° C.

EXAMPLE 13

N-Aminoiminomethyl-S-(2-Chloroethyl)-Isothiuronium Bromide 14.9 g (0.05 mole) of N-aminoiminomethyl-thiourea carbonate are added to 50 ml of anhydrous ethanol. To the suspension thus obtained 17.2 g (0.12 mole) of 1-bromo-2-chloro-ethane are added and the reaction mixture is heated to boiling under intensive stirring. The reaction mixture is refluxed for 90 minutes and cooled to room temperature. The mixture is filtered in order to remove the eventually precipitated substance. The clear filtrate is evaporated in vacuo. The oily residue is crystallized from ethyl acetate. The precipitated white crystals are filtered and dried at 40°–50° C. Thus 17.2 g of the desired compound are obtained, yield 66%, mp.: 142°–143° C.

EXAMPLE 14

N-Aminoiminomethyl-S-(1-Chloro-2-Hydroxy-Propyl)-Isothiuronium Bromide 14.9 g (0.05 mole) of N-aminoiminomethyl-thiourea carbonate are added to 50 ml of anhydrous ethanol. To the suspension thus obtained 20.8 g (0.12 mole) of 1-bromo-2-hydroxy-3-chloro-propane are added. The reaction mixture is slowly heated to boiling under vigorous stirring. The reaction mixture is refluxed for 90 minutes and cooled to room temperature. The mixture is filtered in order to remove the eventually precipitated substance. The clear filtrate is evaporated in vacuo. The oily residue is crystallized from ethyl acetate. The precipitated slightly creme-colored crystals are filtered and dried at 40°–50° C. Thus 17.8 g of the desired compound are obtained, yield 61%. Mp.: 118°–119° C.

EXAMPLE 15

N-Aminoiminomethyl-S-(3-Chloropropyl)-Isothiuronium Bromide 14.9 g (0.05 mole) of N-aminoiminomethyl-thiourea carbonate are added to 80 ml of acetonitrile. To the suspension thus obtained 18.9 g (0.12 mole) of 1-bromo-3-chloro-propane are added and the reaction mixture is slowly heated to boiling under vigorous stirring. The reaction mixture is refluxed for 90 minutes, the solid substance is removed by filtering the hot reaction mixture and the filtrate is allowed to cool to room temperature. The precipitated white crystals are filtered and dried at 40°–50° C. Thus 17.3 g of the desired compound are obtained, yield 65%. Mp.: 129°–131° C.

EXAMPLE 16

N-Aminoiminomethyl-S-(2-Hydroxyethyl)-Isothiuronium Chloride 14.9 g (0.05 mole) of N-aminoiminomethyl-thiourea carbonate are added to 50 ml of anhydrous ethanol. To the suspension 9.7 g (0.12 mole) of ethylene chlorohydrine are added and the reaction mixture is slowly heated to boiling under vigorous stirring. The reaction mixture is refluxed for 90 minutes and cooled to room temperature. The mixture is filtered in order to remove the eventually precipitated substance and the clear filtrate is evaporated in vacuo. The oily residue is crystallized from ethyl acetate. The crystals are filtered and dried at 40°–50° C. Thus 13.5 g of the desired compound are obtained, yield 68%. Mp.: 134°–136° C.

EXAMPLE 17

N-Aminoiminomethyl-S-Glycidyl-Isothiuronium Bromide 14.9 g (0.05 mole) of N-aminoiminomethyl-thiourea carbonate are added to 80 ml of acetonitrile. To the suspensiton thus obtained 16.5 g (0.12 mole) of epibromo hydrine are added and the reaction mixture is slowly heated to boiling under vigorous stirring. The reaction mixture is refluxed for 2 hours and filtered until hot. The clear filtrate is allowed to cool to room temperature. The precipitated white crystals are filtered and dried at 40°–50° C. Thus 13.5 g of the desired compound are obtained, yield 53%. Mp.: 138°–139° C.

EXAMPLE 18

N-Aminoiminomethyl-S-Benzyl-Thiuronium Chloride 14.9 g (0.05 mole) of N-aminoiminomethyl-thiourea carbonate are added to 50 ml of anhydrous ethanol. To the suspension thus obtained 15.2 g (0.12 mole) of benzyl chloride are added and the reaction mixture is heated to boiling under vigorous stirring. The reaction mixture is refluxed for an hour and cooled to room temperature. The mixture is filtered in order to remove the eventually precipitated substance. The clear filtrate is evaporated in vacuo and the oily residue is crystallized from ethyl acetate. The precipitated white crystals are filtered and dried at 40°–50° C. Thus 19.1 g of the desired compound are obtained, yield 78%. Mp.: 159°–161° C.

EXAMPLE 19

The isothiuronium salts prepared according to Examples 9–18 can be recrystallized by the following method, if desired. The process is shown by using N-aminoiminomethyl-S-allyl-isothiuronium chloride.

10 g of N-aminoiminomethyl-S-allyl-isothiuronium chloride are added to 60 ml of a 5:1 mixture of ethanol and methanol. The small amount of undissolved crystals is removed by filtering the hot mixture. The filtrate is clarified with activated charcoal, if necessary. The clear filtrate is allowed to cool to room temperature, whereby white crystals precipitate. The mixture is cooled to 0°–5° C., allowed to stand at this temperature for an hour and filtered. The crystals are washed with icecold ethanol and dried at 40°–50° C. Thus 8.1 g of the desired compound are obtained, yield 81%.

EXAMPLE 20

N-Aminoiminomethyl-N'-Methyl-S-Allyl-Isothiuronium Chloride 16.3 g (0.05 mole) of N-aminoiminomethyl-N'-methyl-thiourea carbonate prepared according to Example 2 are added to 50 ml of anhydrous ethanol. To the suspension thus obtained 9.18 g (0.12 mole) of allyl chloride are added and the reaction mixture is heated to boiling under vigorous stirring. The reaction mixture is refluxed for an hour and cooled to room temperature. The mixture is filtered in order to remove the eventually precipitated substance. The clear filtrate is evaporated in vacuo. The oily residue is crystallized from ethyl acetate. The white crystals are filtered and dried at 40°–50° C. Thus 13.6 g of the desired compound are obtained, yield 61%. Mp.: 137°–139° C.

EXAMPLE 21

N-aminoiminomethyl-N'-Isopropyl-S-Allyl-Isothiuronium Chloride 19.1 g (0.05 mole) of N-aminoiminomethyl-N'-isopropyl-thiourea carbonate prepared according to Example 5, are added to 50 ml of anhydrous ethanol. To the suspension thus obtained 9.18 g (0.12 mole) of allyl chloride are added and the reaction mixture is heated to boiling under vigorous stirring. The reaction mixture is refluxed for an hour and cooled to room temperature. The mixture is filtered in order to remove the eventually precipitated substance. The clear filtrate is evaporated in vacuo and the oily residue is crystallized from ethyl acetate. The precipitated white crystals are filtered and dried at 40°–50° C. Thus 13.3 g of the desired compound are obtained, yield 56%. Mp.: 134°–135° C.

EXAMPLE 22

N-Aminoiminomethyl-N'-Cyclohexyl-S-Allyl-Isothiuronium Chloride 23.1 g (0.05 mole) of N-aminoiminomethyl-N'-cyclohexyl-thiourea carbonate prepared according to Example 8 are added to 50 ml of anhydrous ethanol. To the suspension thus obtained 9.18 g (0.12 mole) of allyl chloride are added and the reaction mixture is heated to boiling under vigorous stirring. The reaction mixture is refluxed for an hour and cooled to room temperature. The mixture is filtered in order to remove the eventually precipitated substance and the clear filtrate is evaporated in vacuo. The oily residue is crystallized from ethyl acetate. The precipitated white crystals are filtered and dried at 40°–50° C. Thus 20.85 g of the desired compound are obtained, yield 85%. Mp.: 129°–130° C.

EXAMPLES 23–31

In an analogous manner to Example 12 the following isothiuronium compounds of the Formula I are prepared:

23. N-aminoiminomethyl-S-ethyl-isothiuronium bromide, mp.: 123°–124° C.;
24. N-aminoiminomethyl-S-isopropyl-isothiuronium bromide, mp.: 120°–122° C.;
25. N-aminoiminomethyl-S-n-butyl-isothiuronium bromide, mp.: 116°–118° C.;
26. N-aminoiminomethyl-S-isoamyl-isothiuronium bromide, mp.: 111°–113° C.;
27. N-aminoiminomethyl-S-(2-bromo-ethyl)-isothiuronium bromide, mp.: 129°–131° C.;

28. N-aminoiminomethyl-S-(3-bromo-propyl)-isothiuronium bromide, mp.: 127°–129° C.;
29. N-aminoiminomethyl-S-(3-hydroxy-propyl)-isothiuronium bromide, mp.: 132°–135° C.;
30. N-aminoiminomethyl-S-(3-mercapto-propyl)-isothiuronium bromide, mp.: 141°–142° C.;
31. N-aminoiminomethyl-S-propargyl-isothuronium bromide, mp.: 131°–133° C.

EXAMPLES 32–40

In an analogous manner to Example 20 the following compounds are prepared:
32. N-aminoiminomethyl-N'-methyl-S-(2-hydroxyethyl)-isothiuronium bromide, mp.: 147°–148° C.;
33. N-aminoiminomethyl-N'-ethyl-S-(2-chloroethyl)-isothiuronium bromide, mp.: 143°–144° C.;
34. N-aminoiminomethyl-N'-ethyl-S-allyl-isothiuronium chloride, mp.: 138°–139° C.;
35. N-aminoiminomethyl-N'-isopropyl-S-(3-chloropropyl)-isothiuronium bromide, mp.: 140°–142° C.;
36. N-aminoiminomethyl-N'-isopropyl-S-methallyl-isothiuronium chloride, mp.: 138°–139° C.;
37. N-aminoiminomethyl-N'-cyclohexyl-S-n-propyl-isothiuronium bromide, mp.: 133°–135° C.;
38. N-aminoiminomethyl-N'-cyclohexyl-S-methallyl-isothiuronium chloride, mp.: 130°–132° C.;
39. N-aminoiminomethyl-N'-cyclohexyl-S-glycidyl-isothiuronium bromide, mp.: 143°–145° C.;
40. N-aminoiminomethyl-N'-cyclohexyl-S-benzyl-isothiuronium chloride, mp.: 147°–149° C.

The melting point and IR spectrum of the compounds of the Formula I are summarized in the following Table VIII.

TABLE VIII

| R² | R¹ | X | Op(°C.) | Characterized peaks of IR spectrum |
|---|---|---|---|---|
| H | methyl | J | 124–125 | 3300, 3120, 1685, 1570 |
| H | n-propyl | Br | 122–124 | 3300, 3120, 2925, 2850, 1685, 1570, 730 |
| H | allyl | Br or Cl | 123–125 | 3290, 3260, 3160, 3105, 1640, 1605, 1550, 1375, 1090, 980, 910, 705, 650 |
| H | 2-chloroethyl | Br | 142–143 | 3300, 3110, 2925, 1640, 920, 720, |
| H | 1-chloro-2-hydroxy-propyl | Br | 118–119 | 3300, 3110, 3000, 2850, 1685, 1610, 720 |
| H | 3-chloro-propyl | Br | 129–131 | 3300, 3275, 3165, 3105, 2900, 2825, 1680, 695 |
| H | 2-hydroxy-ethyl | Cl | 134–136 | 3310, 3280, 3110, 3000, 2990, 1675, 1610, |
| H | glycidyl | Br | 138–139 | 3300, 3275, 3110, 3000, 1690, 1600 865, |
| H | benzyl | Cl | 159–161 | 3290, 3280, 3115, 3005, 1680, 1590, 1485, 755 |
| H | ethyl | Br | 123–124 | 3300, 3120, 1685, 1570, |
| H | isopropyl | Br | 120–122 | 3300, 3120, 1680, 1380, 1365 |
| H | n-butyl | Br | 116–118 | 3315, 3300, 3210, 3180, 2850, 1690, 1450 |
| H | isoamyl | Br | 111–113 | 3305, 3300, 3205, 3175, 2960, 2845, 1695, 1470 |
| H | 2-bromo-ethyl | Br | 129–131 | 3300, 3205, 2910, 1670, 1090, 715 |
| H | 3-bromo-propyl | Br | 127–129 | 3305, 3215, 2920, 1665 |
| H | 3-hydroxy-propyl | Br | 132–135 | 3590, 3300, 3220, 2925, 1680 |
| H | 3-mercapto-propyl | Br | 141–142 | 3320, 3305, 3210, 3180, 2920, 2570, 1690 |
| H | propargyl | Br | 131–133 | 3310, 3300, 3200, 2180, 1680 |
| methyl | allyl | Cl | 137–139 | 3305, 3290, 2960, 2690, 1640 |
| methyl | 2-hydroxy-ethyl | Br | 147–148 | 3585, 3300, 3285, 1680, 1375, 1360 |
| ethyl | 2-chloro-ethyl | Br | 143–144 | 3305, 3285, 2965, 1660, 765 |
| ethyl | allyl | Cl | 138–139 | 3310, 3300, 3210, 3180, 1650, 990, 905 |
| isopropyl | allyl | Cl | 134–135 | 3305, 3295, 3200, 3170, 1655, 985, 895 |
| isopropyl | methallyl | Cl | 138–139 | 3305, 3295, 3200, 3175, 1650, 890 |
| isopropyl | 3-chloro-propyl | Br | 140–142 | 3320, 3300, 3195, |

TABLE VIII-continued

| R² | R¹ | X | Op(°C.) | Characterized peaks of IR spectrum |
|---|---|---|---|---|
| cyclohexyl | allyl | Cl | 129–130 | 3160, 1690, 775 |
| cyclohexyl | n-propyl | Br | 133–135 | 3315, 3305, 3200, 3170, 2830, 1695, 985, 900 |
| cyclohexyl | methallyl | Cl | 130–132 | 3320, 3300, 3210, 3175, 2925 |
| cyclohexyl | glycidyl | Br | 143–145 | 3315, 3300, 3215, 3180, 885 |
| cyclohexyl | benzyl | Cl | 147–149 | 3325, 3315, 3210, 3190, 1690, 870 |
| | | | | 3300, 3275, 3120, 3000, 1675, 1590, 750. |

EXAMPLE 41

Preparation of Tablets and Dragées

Tablets and dragées are prepared in pressing machine equipped with an automatic feeder. The active ingredient is previously granulated with suitable auxiliary agents by means of the dry or wet procedure. If wet granules are prepared, the granules are preferably dried in vacuo. The granules used for the preparation of tablets or dragée core are pressed through a suitable metal-free sieve. For the preparation of granules preferably a granule simplex composition according to the Pharmacopiea or other suitable composition may be used. Tablets and dragée cores comprising 30 mg of the active ingredient are prepared and 70 mg of vehiculum (e.g. granulatum simplex) are added.

EXAMPLE 42

Preparation of Capsules

Preferably automatic filling machines are used. The active ingredient is granulated with suitable auxiliary agents (e.g. granulatum simplex) or any other inert additive. The granules are brought to suitable particle size, sieved and filled into capsules. The active ingredient content of the capsules amounts to 30 mg.

EXAMPLE 43

Preparation of Powder Ampoules

No separate auxiliary agents are used in the preparation of the powder ampoules. The active ingredient content of the powder ampouls amounts to 10 and 20 mg, respectively. The solvent ampoules contain 1 or 2 ml of distilled water or a physiological saline solution, respectively. It is preferred to dilute with at least 100 ml of an infusion and to use the contents of the ampouls directly after dissolving.

EXAMPLE 44

N-(Aminoiminomethyl)-S-Metallyl-Isothiuronium-Bromide 14.9 g N-(aminoiminomethyl)-thiourea carbonate are suspended in 50 ml of abs. ethanol. 16.1 g of metallyl-bromide are added and the reaction mixture is refluxed for 30 minutes. After filtration the solvent is distilled off in vacuo. 21 g of a honey like product are obtained which cristallizes on standing.

EXAMPLE 45

N-(Aminoiminomethyl)-N'-Allyl-S-Allyl-Isothiuronium Bromide 17.6 g N-(aminoiminomethyl)-N'-allyl-thiourea carbonate are suspended in 50 ml of anhydrous ethanol. 14.5 g of allyl-bromide are added and the reaction mixture is refluxed while stirring intensively for 1 hour whereupon the mixture is filtered and the solvent is distilled off in vacuo. 23 g of an oily viscous product are obtained.

EXAMPLE 46

N-Aminoiminomethyl-S-Allyl-Isothiuronium Chloride

A mixture of 4.2 g of dicyane diamide, 20 ml of ethanol saturated with hydrochloric acid and 3.7 g of allyl mercaptane is slowly heated to boiling under vigorous stirring. The reaction mixture is refluxed for 3 hours and cooled to 0° C. The precipitated crystals are filtered off and washed with ethanol. Thus 7 g of the desired compound are obtained. Mp.: 125°–127° C.

What we claim is:

1. A salt of the Formula (I)

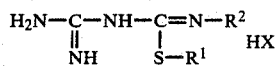

wherein
R¹ is allyl, 2-chloroethyl, 2-chloro-2-hydroxypropyl, 3-chloropropyl, 2-hydroxyethyl, glycidyl, 2-bromoethyl, 3-bromopropyl, 3-hydroxypropyl, 3-mercapto-propyl, propargyl, methallyl, or 1-chloro-2-hydroxy-propyl;
R² is hydrogen, $C_1$ to $C_6$ alkyl, $C_2$ to $C_6$ alkenyl, $C_2$ to $C_6$ alkynyl, or $C_3$ to $C_6$ cycloalkyl; and
X is halide.

2. The salt of the Formula (I) defined in claim 1 which is an N-aminoiminomethyl-S-allyl-isothiuronium hydrohalide.

3. The salt of the Formula (I) defined in claim 1 which is an N-aminoiminomethyl-S-allyl-isothiuronium hydrobromide.

4. The salt of the Formula (I) defined in claim 1 which is an N-aminoiminomethyl-S-(2-hydroxyethyl)-isothiuronium hydrohalide.

5. The salt of the Formula (I) defined in claim 1 which is an N-aminoiminomethyl-S-(2-hydroxylethyl)-isothiuronium hydrochloride.

6. The salt of the Formula (I) defined in claim 1 which is an N-aminoiminomethyl-S-(3-hydroxyl-propyl)-isothiuronium hydrohalide.

7. The salt of the Formula (I) defined in claim 1 which is N-aminoiminomethyl-S-(3-hydroxylpropyl)-isothiuronium hydrobromide.

8. An immunostimulant, cytostatic or anti-tick pharmaceutical composition which comprises as active ingredient, a therapeutically effective amount of the salt of the Formula (I) as defined in claim 1 in combination with a pharmaceutically acceptable inert carrier.

9. A method of treating a mammalian subject requiring and susceptible to immunostimulant therapy which comprises the step of administering to said mammalian subject a therapeutically effective amount of a salt of the Formula (I)

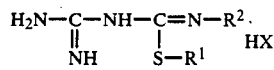

wherein
R$^1$ is C$_1$ to C$_6$ alkyl, C$_2$ to C$_6$ alkenyl, C$_2$ to C$_6$ alkynyl, C$_3$ to C$_6$ cycloalkyl, aralkyl or aryl, which groups can be substituted by at least one oxy, hydroxy, mercapto, or halogen;
R$^2$ is hydrogen, C$_1$ to C$_6$ alkyl, C$_2$ to C$_6$ alkenyl, C$_2$ to C$_6$ alkynyl, or C$_3$ to C$_6$ cycloalkyl; and
X is halide.

10. A method of treating a mammalian subject requiring antitumor therapy which comprises the step of administering to said mammalian subject a therapeutically effective amount of a salt of the Formula (I)

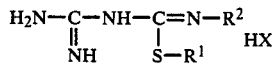

wherein
R$^1$ is C$_1$ to C$_6$ alkyl, C$_2$ to C$_6$ alkenyl, C$_2$ to C$_6$ alkynyl, C$_3$ to C$_6$ cycloalkyl, aralkyl or aryl, which groups can be substituted by at least one oxy, hydroxy, mercapto, or halogen;
R$^2$ is hydrogen, C$_1$ to C$_6$ alkyl, C$_2$ to C$_6$ alkenyl, C$_2$ to C$_6$ alkynyl, or C$_3$ to C$_6$ cycloalkyl; and
X is halide.

11. A method of treating a mammalian subject requiring anti-tick therapy which comprises the step of administering to said mammalian subject a therapeutically effective amount of a salt of the Formula (I)

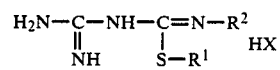

wherein
R$^1$ is C$_1$ to C$_6$ alkyl, C$_2$ to C$_6$ alkenyl, C$_2$ to C$_6$ alkynyl, C$_3$ to C$_6$ cycloalkyl, aralkyl or aryl, which groups can be substituted by at least one oxy, hydroxy, mercapto, or halogen;
R$^2$ is hydrogen, C$_1$ to C$_6$ alkyl, C$_2$ to C$_6$ alkenyl, C$_2$ to C$_6$ alkynyl, or C$_3$ to C$_6$ cycloalkyl; and
X is halide.

12. A salt of the Formula (I)

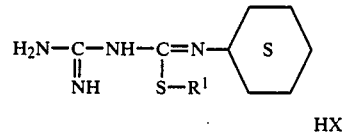

wherein
R$^1$ is C$_1$ to C$_6$ alkyl or benzyl; and
X is halide.

13. An N-aminoiminomethyl-S-isoamyl-isothiuronium hydrohalide.

* * * * *

UNITED STATES PATENT AND TRADEMARK OFFICE
CERTIFICATE OF CORRECTION

PATENT NO. : 4,710,578

DATED : 1 December 1987

INVENTOR(S) : Csaba VERTESI, et al

It is certified that error appears in the above-identified patent and that said Letters Patent is hereby corrected as shown below:

In Column 11, line 18, for "1-oxypropyl" read --3-hydroxy-propyl--; and

In Claim 1, line 4, for

"2-chloro-2-hydroxypropyl" read --3-chloro-2-hydroxypropyl --.

Signed and Sealed this

First Day of August, 1989

Attest:

DONALD J. QUIGG

Attesting Officer

Commissioner of Patents and Trademarks